(12) United States Patent
Shin et al.

(10) Patent No.: US 11,286,273 B2
(45) Date of Patent: Mar. 29, 2022

(54) RHAMNOLIPID COMPOUNDS AND USE THEREOF

(71) Applicant: KOREA INSTITUTE OF OCEAN SCIENCE & TECHNOLOGY, Busan (KR)

(72) Inventors: Hee Jae Shin, Busan (KR); Byeoung Kyu Choi, Daegu (KR); Hwa Sun Lee, Busan (KR); Hyi Seung Lee, Busan (KR); Yeon Ju Lee, Busan (KR); Jong Seok Lee, Busan (KR); Ji Hoon Lee, Busan (KR); Chan Hong Park, Gyeonggi-do (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 0 days.

(21) Appl. No.: 17/257,255

(22) PCT Filed: Mar. 8, 2019

(86) PCT No.: PCT/KR2019/002742
§ 371 (c)(1),
(2) Date: Dec. 30, 2020

(87) PCT Pub. No.: WO2020/158995
PCT Pub. Date: Aug. 6, 2020

(65) Prior Publication Data
US 2021/0355151 A1    Nov. 18, 2021

(30) Foreign Application Priority Data

Jan. 28, 2019    (KR) .................. 10-2019-0010711

(51) Int. Cl.
*C07H 15/04*    (2006.01)
*C07H 1/00*    (2006.01)

(52) U.S. Cl.
CPC .............. *C07H 15/04* (2013.01); *C07H 1/00* (2013.01)

(58) Field of Classification Search
None
See application file for complete search history.

(56) References Cited

PUBLICATIONS

Kristoffersen, Mar. Drugs 2018, 16, 163. (Year: 2018).*

* cited by examiner

*Primary Examiner* — Layla D Berry
(74) *Attorney, Agent, or Firm* — Weisun Rao; Venture Partner, LLC (57) ABSTRACT

Disclosed are a novel rhamnolipid compound, an optical isomer thereof, or a pharmaceutically acceptable salt thereof in the present disclosure. The novel rhamnolipid compound, the optical isomer thereof, or the pharmaceutically acceptable salt thereof selectively exhibits cytotoxicity to human cancer cell lines, thereby inhibiting the growth of cancer cells, and thus has particularly excellent preventive or therapeutic effects against the above-mentioned types of cancers.

12 Claims, 2 Drawing Sheets

1a : R=(S)-MTPA
1b : R=(R)-MTPA

RHAMNOLIPID COMPOUNDS AND USE THEREOF

TECHNICAL FIELD

The present disclosure relates to a novel rhamnolipid compound and use thereof.

BACKGROUND ART

Rhamnolipid is a sugar moiety linked to a β-hydroxy fatty acid chain and belongs to a class of biosurfactants composed of rhamnose. Rhamnolipid is classified into a mono-rhamnolipid containing a single rhamnose sugar ring and a di-rhamnolipid containing two rhamnose sugar rings. These biosurfactants are mainly produced from *Pseudomonas* species such as *P. chlororaphis, P. plantarii, P. putida*, and *P. fluorescens*. During the last three centuries, rhamnolipids have been extensively studied and reviewed due to their biodegradability, reduced toxicity compared to synthetic surfactants, and various applications. Rhamnolipid is known to exhibit surface-active properties such as emulsification, dispersion, foaming, cleaning, wetting and stabilization. Moreover, various studies have demonstrated that rhamnolipid exhibits low toxicity and antibacterial activity. These unique and diverse properties are suitable for use in a wide range of industrial needs, such as biological purification of contaminants, cosmetics, foods, pharmaceuticals and therapeutics.

A marine environment has served as an important reservoir of natural products for new drugs for decades. In particular, marine microorganisms are considered to be efficient producers of leading substances with biomedical potential. Additionally, structurally diverse and impressive bioactive natural products have been identified from marine microbes.

Dokdo in the East Sea of Korea is made up of 89 small islands and rocks, and is a huge volcanic island with rich and well-preserved biological diversity. The present inventors isolated a strain of *Actinoalloteichus hymeniacidonis* 179DD-027 KCTC 13780BP from deep-sea sediment samples collected from the shores of Dokdo. Subsequently, three novel rhamnolipids were identified via fermentation, solvent extraction and chemical investigation procedures of the produced strain, and cytotoxicity of the novel rhamnolipid against cancer cell lines was identified. Thus, the present disclosure was completed.

Prior Technical Literature

Patent Literature

Korean Patent Application Publication No. 10-2002-0016707

DISCLOSURE

Technical Purpose

A purpose of the present disclosure is to provide a novel rhamnolipid compound, an optical isomer thereof, or a pharmaceutically acceptable salt thereof.

Further, a purpose of the present disclosure is to provide use of the novel rhamnolipid compound, the optical isomer thereof or the pharmaceutically acceptable salt thereof.

Technical Solution

Compound of Chemical Formula 1

In order to achieve the above-described technical purpose, the present disclosure provides a novel rhamnolipid compound of following Chemical Formula 1, an optical isomer thereof, or a pharmaceutically acceptable salt thereof:

[Chemical Formula 1]

Wherein in Chemical Formula 1,
n is 1 or 2, and R is

Specifically, Chemical Formula 1 is the same as following Chemical Formula 2 when n is 1:

[Chemical Formula 2]

Wherein in Chemical Formula 2, R is

Further, Chemical Formula 1 is the same as a following Chemical Formula 3 when n is 2:

[Chemical Formula 3]

Wherein in Chemical Formula 3, R

According to an embodiment of the present disclosure, the compound of Chemical Formula 1 may be one selected from a group consisting of following compounds:

17-hydroxy-3-(3,4,5-trihydroxy-6-methyltetrahydro-2H-pyran-2-yloxy)octadecanoic acid; 17-oxo-3-(3,4,5-trihydroxy-6-methyltetrahydro-2H-pyran-2-yloxy)octadecanoic acid; and 3-(4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

The compound represented by Chemical Formula 1 in accordance with the present disclosure may contain one or more asymmetric carbons. Accordingly, the compound may be present as a racemate, a racemic mixture, a single enantiomer, a diastereomeric mixture and each diastereomer.

The isomer, that is, the compound represented by Chemical Formula 1 may be separated, for example, using conventional techniques such as column chromatography or HPLC. Alternatively, a stereoisomer of each of the compounds represented by Chemical Formula 1 may be stereospecifically synthesized using an optically pure starting material and/or reagent of a known arrangement.

Specifically, the compound of Chemical Formula 1 may be one selected from a group consisting of following compounds:

(17R)-17-hydroxy-3-((2 S)-3,4,5-trihydroxy-6-methyltetrahydro-2H-pyran-2-yloxy)octadecanoic acid; 17-oxo-3-((2S)-3,4,5-trihydroxy-6-methyltetrahydro-2H-pyran-2-yloxy)octadecanoic acid; and (17R)-3-((2S)-4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

Further, according to an embodiment of the present disclosure, the compound of Chemical Formula 1 may be one selected from a group consisting of compounds of a following Table 1.

TABLE 1

| Example | Structure |
|---------|-----------|
| 1 | (structure with sugar moiety linked via O to a long aliphatic chain bearing OH at C1', carbonyl, and terminal OH at C17') |
| 2 | (structure with sugar moiety linked via O to a long aliphatic chain with OH, carbonyl, and terminal methyl ketone) |
| 3 | (structure with disaccharide moiety linked via O to a long aliphatic chain with OH, carbonyl, and terminal OH) |

In the present disclosure, the pharmaceutically acceptable salt refers to a salt commonly used in the pharmaceutical industry. For example, the pharmaceutically acceptable salt may include inorganic ion salts made of calcium, potassium, sodium and magnesium; inorganic acid salts made of hydrochloric acid, nitric acid, phosphoric acid, bromic acid, iodic acid, perchloric acid and sulfuric acid; organic acid salts made of acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like; sulfonic acid salts made of methanesulfonic acid, ethanesulfonic acid, benzenesulfonic acid, p-toluenesulfonic acid and naphthalenesulfonic acid; amino acid salts made of glycine, arginine, lysine, etc.; and amine salts made of trimethylamine, triethylamine, ammonia, pyridine, picoline, etc. However, types of salts meant in the present disclosure are not limited to these listed salts.

Method for Preparing Compound of Chemical Formula 1

The present disclosure provides a method for preparing a compound of Chemical Formula 1, an optical isomer thereof, or a pharmaceutically acceptable salt thereof, the method including separating the compound represented by Chemical Formula 1, the optical isomer thereof or the pharmaceutically acceptable salt thereof from *Actinoalloteichus hymeniacidonis* 179DD-027 KCTC 13780BP or a culture thereof.

In the present disclosure, the culture of *Actinoalloteichus hymeniacidonis* 179DD-027 KCTC 13780BP may be obtained by culturing the strain in a liquid medium or a solid medium. The medium may contain, but not limited to, glucose, starch syrup, dextrin, starch, molasses, animal oil, or vegetable oil as a carbon source. Further, the medium may contain, but not limited to, bran, soybean meal, wheat, malt, cottonseed meal, fish meal, corn tip liquor, gravy, yeast extract, ammonium sulfate, sodium nitrate or urea as a nitrogen source. Further, the medium may contain table salt, potassium, magnesium, cobalt, chlorine, phosphoric acid, sulfuric acid, or other inorganic salts that promote ion generation, if necessary. The culture may be shaking or stationary culture. A culture temperature may be about 20° C. to about 37° C., preferably about 25° C. to about 30° C.

The compound of Chemical Formula 1 may be obtained by solvent extraction, concentration, and column chromatography of the strain or the culture thereof. The concentration may be carried out by evaporating an extract under reduced pressure while adding a solvent to the strain or a culture thereof. The solvent may be ethyl acetate, a lower alcohol having 1 to 4 carbon atoms, and preferably ethyl acetate. The chromatography may be column chromatography, plate chromatography, paper chromatography, or thin film chromatography depending on a type of a stationary phase. Alternatively, the chromatography may be HPLC (high performance liquid chromatography) or gas chromatography based on the physical properties of the mobile phase.

According to an embodiment of the present disclosure, an ethyl acetate extract of a strain or a culture thereof may be subjected to fractionation using flash column chromatography, and then may be purified by HPLC using a mixed solvent of methanol and water. Thus, the compound of Chemical Formula 1 may be obtained.

Therefore, the present disclosure provides a method for preparing a compound of Chemical Formula 1, an optical isomer thereof, or a pharmaceutically acceptable salt thereof, the method including (a) culturing *Actinoalloteichus hymeniacidonis* 179DD-027 KCTC 13780BP; (b) centrifuging a culture fluid of the (a) to separate supernatant; (c) extracting the supernatant of the (b) with ethyl acetate; and (d) stepwise eluting the ethyl acetate extract of the (c) with MeOH/$H_2O$.

The preparation method of the compound of Chemical Formula 1, the optical isomer thereof or the pharmaceutically acceptable salt thereof according to the present disclosure comprises (a) culturing *Actinoalloteichus hymeniacidonis* 179DD-027 KCTC 13780BP. The culture in the (a) may be carried out at a culture temperature of about 20° C. to about 37° C. and preferably of about 25° C. to about 30° C. under the above-mentioned conventional culture medium condition.

The method for preparing the compound of Chemical Formula 1, the optical isomer thereof, or the pharmaceutically acceptable salt thereof according to the present disclosure comprises (b) separating a supernatant by centrifuging the culture fluid of the (a). For separation between the supernatant and *Actinoalloteichus hymeniacidonis* grown in the (a), the supernatant is separated under a conventional centrifugation condition for cell separation.

The method for preparing the compound of Chemical Formula 1, the optical isomer thereof, or the pharmaceutically acceptable salt thereof according to the present disclosure comprises (c) extracting the supernatant of the (b) with ethyl acetate. Extraction preferably comprises treating the supernatant with ethyl acetate at a temperature of 10° C. to 40° C., preferably at room temperature.

The preparation method of the compound of Chemical Formula 1, the optical isomer thereof or the pharmaceutically acceptable salt thereof according to the present disclosure comprises (d) stepwise eluting the ethyl acetate extract of the (c) with MeOH/$H_2O$. Elution with MeOH/$H_2O$ according to the present disclosure comprises performing elution at a sequential concentration. Although not limited thereto, for example, when a ratio of MeOH and $H_2O$ is 1:4, 2:3, 3:2, and 4:1 solvent weight ratio and a 100% methanol solvent is used. Thus, a fraction is obtained via sequential elution, and the compound of Chemical Formula 1 according to the present disclosure is separated therefrom.

In order to separate a compound of Chemical Formula 1, the method of preparing a compound of Chemical Formula 1, an optical isomer thereof, or a pharmaceutically acceptable salt thereof according to the present disclosure may further comprise (e) eluting the fraction eluted in the (d) with an isocratic solvent, and purifying the separated compound of Chemical Formula 1. Eluting the fraction eluted in the (d) with an isocratic solvent may comprise eluting the fraction with an isocratic solvent such as an aqueous acetonitrile solution. For separation and purification, the compound may be separated using a conventional HPLC instrument, chromatography, or the like. According to an embodiment of the present disclosure, the compound of Chemical Formula 1 according to the present disclosure may be isolated and purified using reversed-phase HPLC.

Use of Compound of Chemical Formula 1

The present disclosure provides use of a rhamnolipid compound represented by a following Chemical Formula 1, an optical isomer thereof, or a pharmaceutically acceptable salt thereof:

[Chemical Formula 1]

Wherein in Chemical Formula 1, n is 1 or 2, and R is

The present disclosure provides a pharmaceutical composition including the rhamnolipid compound of Chemical Formula 1, the optical isomer thereof, or the pharmaceutically acceptable salt thereof.

The present disclosure provides a pharmaceutical composition for preventing or treating cancer, the composition including the rhamnolipid compound of Chemical Formula 1, the optical isomer thereof, or the pharmaceutically acceptable salt thereof.

Non-limiting examples of cancer in the present disclosure may include pseudomyxoma, intrahepatic biliary tract cancer, hepatoblastoma, liver cancer, thyroid cancer, colon cancer, testicular cancer, myelodysplastic syndrome, glioblastoma, oral cancer, cleft lip cancer, mycosis fungoides, acute myelogenous leukemia, acute lymphocytic leukemia, basal cell carcinoma, ovarian cancer, ovarian epithelial carcinoma, ovarian germ cell carcinoma, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, diffuse giant B-cell lymphoma, barter bulge cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, pediatric brain cancer, pediatric lymphoma, pediatric leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, mesothelioma, rectal cancer, rectal carcinoma, vaginal cancer, spinal carcinoma, auditory nerve sheath, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, thymic cancer, or the like.

The pharmaceutical composition according to the present disclosure may further contain at least one pharmaceutically acceptable carrier for administration thereof in addition to the rhamnolipid compound of Chemical Formula 1, the optical isomer thereof, or the pharmaceutically acceptable salt thereof. Pharmaceutically acceptable carriers may include saline, sterile water, Ringer's solution, buffered saline, dextrose solution, maltodextrin solution, glycerol, ethanol, and mixtures of one or more of these components. If necessary, other conventional additives such as antioxidants, buffers, and bacteriostatic agents may be added thereto. In addition, diluents, dispersants, surfactants, binders, and lubricants may be additionally added to prepare injectable formulations such as aqueous solutions, suspensions, emulsions, and pills, capsules, granules, or tablets. Accordingly, the pharmaceutical composition according to the present disclosure may be a patch, liquid, pill, capsule, granule, tablet, suppository, or the like. These formulations may be prepared by conventional methods used for formulation in the art or by methods disclosed in Remington's Pharmaceutical Science (latest edition), Mack Publishing Company, Easton Pa., and formulated into various formulations depending on each disease or ingredient.

The pharmaceutical composition according to the present disclosure may be administered orally or parenterally (for example, intravenously, subcutaneously, intraperitoneally or topically) according to a desired method. The dosage range varies according to the patient's weight, age, sex, health status, diet, administration time, administration method, excretion rate, and disease type, severity, and the like. The daily dosage of the compound of Chemical Formula 1 according to the present disclosure may be about 0.01 mg/kg to 1,000 mg/kg, preferably 0.1 mg/kg to 100 mg/kg, and the compound may be administered once or several times a day.

The pharmaceutical composition according to the present disclosure may further contain one or more active ingredients exhibiting the same or similar medicinal efficacy in addition to the rhamnolipid compound of Chemical Formula 1, the optical isomer thereof, or the pharmaceutically acceptable salt thereof.

The present disclosure provides a method for cancer treatment or prevention, the method including administering a therapeutically effective amount of the rhamnolipid compound of Chemical Formula, the optical isomer thereof, or the pharmaceutically acceptable salt thereof to a mammal including humans.

The term "therapeutically effective amount" used in the present disclosure refers to the amount of the rhamnolipid compound of Chemical Formula 1, the optical isomer thereof, or the pharmaceutically acceptable salt thereof which is effective for the prevention or treatment of cancer. In other words, the therapeutically effective amount may mean an appropriate amount very sufficient to deliver the desired effect, sufficiently preventing serious side effects within the scope of medical judgment. The amount of the rhamnolipid compound of Chemical Formula 1, the optical isomer thereof, or the pharmaceutically acceptable salt thereof according to the present disclosure may be appropriately adjusted in consideration of the route of administration and the administration subject.

The treatment method of the present disclosure includes not only dealing with the disease itself before the onset of symptoms, but also inhibiting or avoiding the symptoms thereof by administering the compound of Chemical Formula 1. In the management of a disease, the prophylactic or therapeutic dose of a particular active ingredient will vary depending on the nature and severity of the disease or condition, and the route along which the active ingredient is administered. The dose and the dosing frequency will vary depending on the age, weight and response of the individual patient. A suitable dosage regimen may be readily selected by one of ordinary skill in the art while taking these factors into account. Further, the treatment method of the present disclosure may further include administration of a therapeutically effective amount of an additional active agent useful for disease treatment together with the compound of Chemical Formula 1. The additional active agent may exhibit a synergistic effect or an auxiliary effect with the compound of Chemical Formula 1.

The present disclosure provides a food composition for preventing or ameliorating cancer, the composition containing the rhamnolipid compound of Chemical Formula 1, the optical isomer thereof, or the pharmaceutically acceptable salt thereof.

The food composition according to the present disclosure may be used as a health functional food. The term "health functional food" means a food prepared and processed using raw materials or ingredients having useful functions for the human body in accordance with No. 6727 of the Health Functional Food Act. The term "functional" refers to ingestion for the purpose of obtaining useful effects for health purposes such as controlling nutrients or physiological effects on the structure and function of the human body.

The food composition according to the present disclosure may contain conventional food additives. Unless otherwise specified, the suitability for the "food additive" may be determined based on the standards and the criteria for the item according to the general test method and the general rules of the food additive code approved by the Food and Drug Administration.

The food composition according to the present disclosure may contain 0.01% to 95%, preferably 1% to 80% by weight of the compound of Chemical Formula 1 with respect to a total weight of the composition for the purpose of preventing and/or ameliorating cancer. Further, for the purpose of preventing and/or ameliorating cancer-related diseases, the food composition may be formulated and processed in the form of tablets, capsules, powders, granules, liquids, pills, beverages, and the like.

Further, the present disclosure is intended to provide the use of the rhamnolipid compound of Chemical Formula 1, the optical isomer thereof, or the pharmaceutically acceptable salt thereof for preparation of a drug for the treatment of cancer. The compound of Chemical Formula 1 for preparation of a drug may be mixed with acceptable adjuvants, diluents, carriers, etc., and may be prepared as a complex formulation together with other active agents to have a synergistic effect of active ingredients.

The present disclosure also provides a method for treating cancer, the method including administering a therapeutically effective amount of the rhamnolipid compound of Chemical Formula 1, the optical isomer thereof, or the pharmaceutically acceptable salt thereof to a subject in need thereof.

The "administration" means providing the rhamnolipid compound of Chemical Formula 1, the optical isomer thereof, or the pharmaceutically acceptable salt thereof according to the present disclosure to a subject by any suitable method. In this connection, the subject refers to an animal, and typically may be a mammal that may have a beneficial effect from treatment using the rhamnolipid compound of Chemical Formula 1 according to the present disclosure, the optical isomer thereof, or the pharmaceutically acceptable salt thereof. Preferred examples of the subject may include primates such as humans.

The present disclosure also provides a composition including the rhamnolipid compound of Chemical Formula 1, the optical isomer thereof, or the pharmaceutically acceptable salt thereof for use in the prevention or treatment of cancer.

The present disclosure also provides use of the composition including the rhamnolipid compound of Chemical Formula 1, the optical isomer thereof, or the pharmaceutically acceptable salt thereof for producing a drug for preventing or treating cancer.

The matters mentioned in the composition, use, and treatment method of the present disclosure are the same as long as they do not contradict each other.

Advantageous Effects

The novel rhamnolipid compound according to the present disclosure, the optical isomer thereof, or the pharmaceutically acceptable salt thereof selectively exhibits cytotoxicity to cancer cell lines, and thus has excellent preventive or therapeutic effects against the above-mentioned types of cancers.

MODES OF THE INVENTION

Hereinafter, an example of the present disclosure will be described in detail so that a person having ordinary knowledge in the technical field to which the present disclosure belongs may easily implement the present disclosure. However, the present disclosure may be implemented in various forms and is not limited to the examples described herein.

Example 1. Production of Rhamnolipid Compound

Experimental Device 1D ($^1$H and $^{13}$C), 2D (COSY, ROESY, HSQC, HMBC) NMR spectra were obtained using a Bruker 600 MHz spectrometer. The UV spectrum was obtained using a Shimadzu UV-1650PC spectrophotometer. The IR spectrum was obtained using a JASCO FT/IR-4100 spectrophotometer. The optical rotation was measured using a Rudolph Research Analytical (Autopol III) polarimeter. High-resolution (HR) ESIMS was recorded using a Shimadzu LC/MS-IT-TOF mass spectrometer. HPLC was performed using an RI-101 (Shodex) detector and a PrimeLine Binary pump. Analytical HPLC was performed on an ODS column (YMC-Pack-ODS-A, 250×4.6 mm, i.d, 5 μm).

Isolation and Mass Culture of 179DD-027 Strain

*Actinoalloteichus hymeniacidonis* 179DD-027 was isolated from sediment samples taken from the coast of Dokdo as an island on the east coast of Korea.

As a result of 16S rRNA gene sequence analysis (GenBank accession number MH681580), the strain was identified as *Actinoalloteichus hymeniacidonis* 179DD-027.

The isolated *Actinoalloteichus hymeniacidonis* 179DD-027 strain was cultured for 7 days at 28° C. in Bennett (BN) agar medium. Afterwards, the strain was inoculated into a flask containing 50 mL of BN liquid medium (containing 10 g of glucose, 1 g of yeast extract, 2 g of tryptone, 1 g of beef extract, 5 g of glycerol and 32 g of NaCl in 1 L of distilled water) and cultured at 130 rpm for 4 days at 28° C. while stirring the medium. 10 mL of the culture fluid was inoculated into a 2 L flask containing a culture medium (1 L) and cultured for 4 days under the same conditions. For mass cultivation, inoculation was performed using a 2 L flask containing 1 L of the culture medium, and cultured at 40 L in BN medium of a 100 L fermenter. 40 L of the culture fluid was incubated at 28° C. for 7 days.

The *Actinoalloteichus hymeniacidonis* 179DD-027 was deposited on the Korea Research Institute of Bioscience and Biotechnology on Dec. 20, 2018, and received the deposit number KCTC 13780BP.

Separation of Compound

The culture fluid (total 40 L) was centrifuged to separate cells and supernatant, and then the supernatant was extracted with ethyl acetate (EtOAc, 40 L×2) at room temperature. The ethyl acetate extract was dried to obtain a crude extract (3 g). The crude extract was fractionated via flash column chromatography using ODS while eluting stepwise (1:4, 2:3, 3:2, 4:1 and 100% MeOH) using a combination of MeOH/H$_2$O.

The fraction eluted with a ratio of MeOH/H$_2$O of 4:1 was subjected to isocratic elution with 40% ACN aqueous solution, and then to purify by an analytical reversed-phase HPLC (YMC-Pack-ODS-A, 250×4.6 mm, id, 5 μm, flow rate 2.0 mL/min, RI detector). Thus, compound 1 (35.2 mg, $t_R$=14 min), compound 2 (4.5 mg, $t_R$=20 min), and compound 3 (5.8 mg, $t_R$=9 min) in a form of a viscous yellow oil were obtained.

1. 17-hydroxy-3-(3,4,5-trihydroxy-6-methyltetrahydro-2H-pyran-2-yloxy)octadecanoic acid Dark brown oil; $[\alpha]_D^{25}$ −33.3 (c 0.3, MeOH); IR $v_{max}$ 3345, 2918, 2851, 1710, 1646, 1127, 1049 cm$^{-1}$;

UV(MeOH) $\lambda_{max}$ (log ε) 318 (3.09), 218 (3.42) nm; HRES-IMS m/z 485.3094 [M+Na]$^+$ (calcd for 485.3090, $C_{24}H_{46}O_8Na$).

2. 17-oxo-3-(3,4,5-trihydroxy-6-methyltetrahydro-2H-pyran-2-yloxy)octadecanoic acid Dark brown oil; $[\alpha]_D^{25}$ −10.0 (c 0.3, MeOH); IR $\nu_{max}$ 3377, 2910, 2851, 1710, 1371, 1068, 1017 cm$^{-1}$; UV(MeOH) $\lambda_{max}$(log ε) 406 (3.29), 312 (3.50), 238 (3.60) nm; HRESIMS m/z 483.2936 [M+Na]$^+$ (calcd for 483.2934, $C_{24}H_{44}O_8Na$).

3. 3-(4,5-dihydroxy-6-methyl-3-(3,4,5-trihydroxy-6-methyltetrahydro-2H-pyran-)2-yloxy)tetrahydro-(2H-pyran-2-yloxy)-17-hydroxyoctadecanoic acid Dark brown oil; $[\alpha]_D^{25}$ −40.0 (c 0.3, MeOH); IR $\nu_{max}$ 3693, 3328, 2971, 2858, 1632, 1349, 1058, 1010 cm$^{-1}$; UV(MeOH) $\lambda_{max}$ (log ε) 310 (3.15), 216 (3.51) nm; HRESIMS m/z 631.3669 [M+Na]$^+$ (calcd for 631.3669, $C_{30}H_{56}O_{12}Na$).

$^1$H NMR (CD$_3$OD, 600 MHz) and $^{13}$C NMR (CD$_3$OD, 125 MHz) results of compounds 1 to 3 are shown in Table 2 below.

TABLE 2

| Position | 1 | | | 2 | | | 3 | | |
|---|---|---|---|---|---|---|---|---|---|
| | $\delta_C$ | TYPE | $\delta_{H\,(J,\,Hz)}$ | $\delta_C$ | TYPE | $\delta_{H\,(J,\,Hz)}$ | $\delta_C$ | TYPE | $\delta_{H\,(J,\,Hz)}$ |
| 3'-L-rhamnose | | | | | | | | | |
| 1 | 98.9 | CH | 4.80, br s | 98.9 | CH | 4.79, br s | 99.0 | CH | 4.79, br s |
| 2 | 71.2 | CH | 3.75, br s | 71.3 | CH | 3.75, br s | 71.5 | CH | 3.75, br s |
| 3 | 70.9 | CH | 3.60, dd (9.6, 3.5) | 70.9 | CH | 3.60, dd (9.6, 3.3) | 71.2 | CH | 3.60, overlap |
| 4 | 72.5 | CH | 3.35, dd (9.6, 9.6) | 72.5 | CH | 3.35, dd (9.6, 9.6) | 72.5 | CH | 3.35, dd (9.6, 9.6) |
| 5 | 68.7 | CH | 3.65, dq (9.6, 6.3) | 68.7 | CH | 3.65, dq (9.6, 6.2) | 68.8 | CH | 3.65, overlap |
| 6 | 16.2 | CH$_3$ | 1.23, d (6.3) | 16.4 | CH$_3$ | 1.23, d (6.2) | 16.5 | CH$_3$ | 1.23, d (6.2) |
| 1' | 173.9 | C | | 174.6 | C | | 174.0 | C | |
| 2' | 40.0 | CH$_2$ | 2.53, dd (13.7, 7.5) 2.48, dd (13.7, 5.1) | 40.5 | CH$_2$ | 2.52, dd (14.8, 7.2) 2.47, dd (14.8, 5.4) | 40.0 | CH$_2$ | 2.52, dd (14.4, 7.6) 2.48, dd (14.4, 5.1) |
| 3' | 74.2 | CH | 4.08, m | 74.4 | CH | 4.08, m | 74.2 | CH | 4.08, m |
| 4' | 33.1 | CH$_2$ | 1.55, m | 33.1 | CH$_2$ | 1.56, m | 33.1 | CH$_2$ | 1.32, 1.57, m |
| 5' | 24.5 | CH$_2$ | 1.29, m | 24.5 | CH$_2$ | 1.30, m | 24.5 | CH$_2$ | 1.32, 1.58, m |
| 6'-15' | 24.5-29.4 | CH$_2$ | 1.29-1.45, overlap | 24.5-29.4 | CH$_2$ | 1.29-1.45, overlap | 24.5-29.4 | CH$_2$ | 1.29-1.45, overlap |
| 16' | 38.8 | CH$_2$ | 1.39, m | 42.9 | CH$_2$ | 2.47, t (7.4) | 36.9 | CH$_2$ | 1.45, 1.53, m |
| 17' | 67.1 | CH | 3.70, m | 210.8 | C | | 70.9 | CH | 3.70, m |
| 18' | 22.0 | CH$_3$ | 1.13, d (6.2) | 28.3 | CH$_3$ | 2.12, s | 17.8 | CH$_3$ | 1.12, d (6.0) |
| 2-L-rhamnose | | | | | | | | | |
| 1" | | | | | | | 97.5 | CH | 4.79, br s |
| 2" | | | | | | | 71.4 | CH | 3.72, br s |
| 3" | | | | | | | 71.1 | CH | 3.60, overlap |
| 4" | | | | | | | 72.5 | CH | 3.33, dd (9.6, 9.6) |
| 5" | | | | | | | 68.6 | CH | 3.65, overlap |
| 6" | | | | | | | 16.4 | CH$_3$ | 1.23, d (6.2) |

Example 2. Structure Determination of Rhamnose Compound

Planar Structure Analysis

Figure 1:
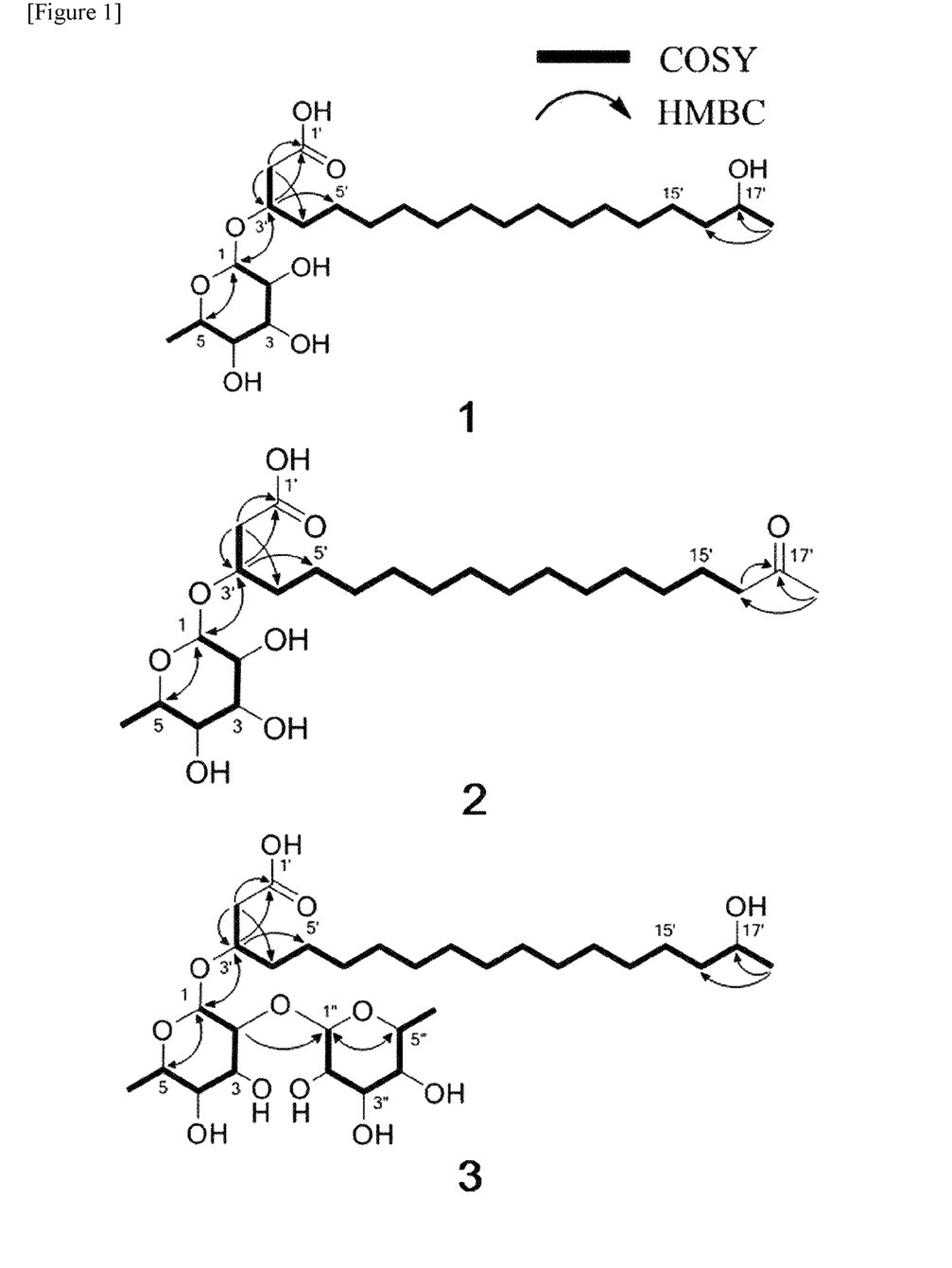
FIG. 1 is a diagram showing COSY and HMBC correlations of compounds 1 to 3.

The planar structure of the compound was determined using 2D NMR data and 1H-1H COSY and HMBC spectra (FIG. 1). In compound 1, the COSY correlation between the terminal methyl groups and highly overlapped protons from $H_2$-2' implies the presence of an aliphatic chain based on the molecular formula. The HMBC correlations between $H_2$-2' and C-1', C-3' and C-4', H-3' and C-1', C-2' and C-5' indicate that the position of the carbonyl carbon C-1' is $\delta_C$ 173.9, and the secondary alcohol H-3' is $\delta_H$ 4.08. Additionally, the chemical shift of H-17' ($\delta_H$ 3.70) and the HMBC correlation between doublet methyl $H_3$-18' to C-17' and C-16' indicate a hydroxy group attached to C-17'. Detailed analysis of the 2D NMR spectrum revealed that the linear hydrated and saturated fatty acid was 3,17-dihydroxyoctadecanoic acid. The hexose moiety was identified based on H-1/C-5 and H-5/C-1 HMBC correlation. The hexose ring was linked to C-3'-OH via an ether linkage based on H-3'/C-1 and H-1/C-3'HMBC correlations. Therefore, it was identified that the planar structure of compound 1 is a new rhamnolipid form.

Figure 2:
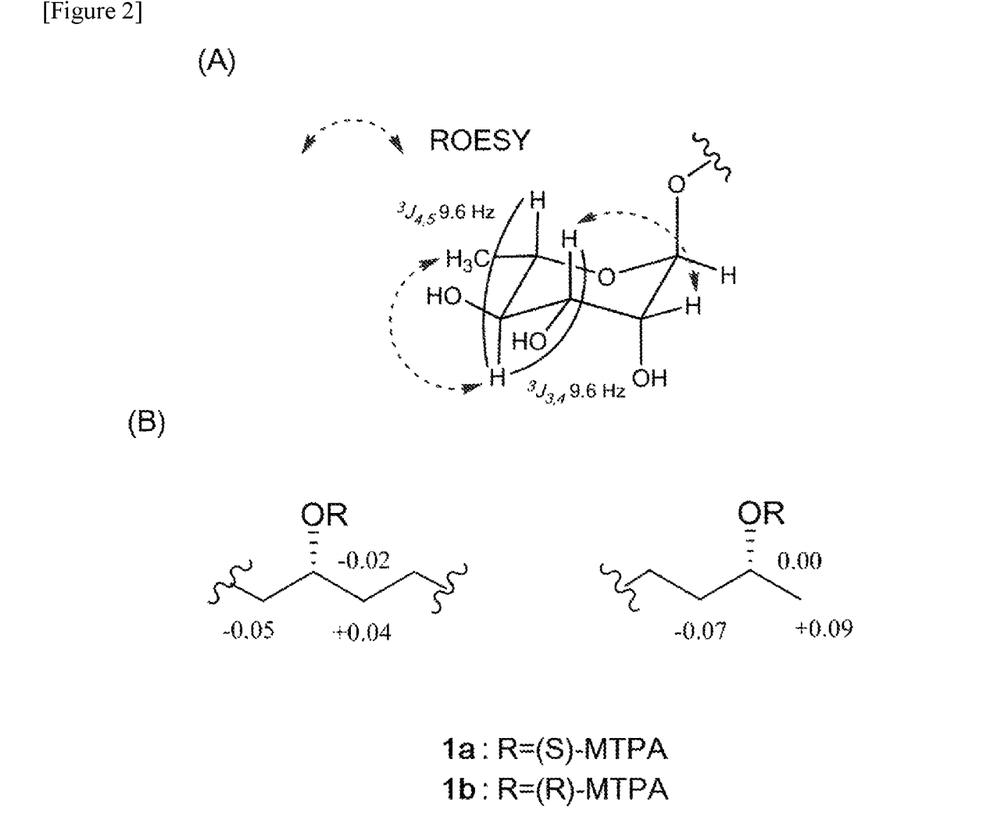
FIG. 2A, is a diagram showing ROESY correlation of sugar moiety of compound 1.
FIG. 2B shows a $\Delta\delta_{S-R}$ value of MPTA ester of methylated aglycone of compound 1 in ppm.

The relative structure of sugar was identified based on a vicinal coupling constant $^3J_{HH}$ and ROESY correlation (FIG. 2). The axial positions of H-3, H-4 and H-5 were assigned due to the presence of large coupling constants ($^3J_{3,4}$=9.6 Hz and $^3J_{4,5}$=9.6 Hz). ROESY correlations between H-2 and H-3, and between H-4 and $H_3$-6 and a broad singlet of an anomer proton at H-1 suggested that the sugar moiety was rhamnose.

Acid hydrolysis of compound 1 provided methylated aglycone and rhamnopyranose of compound 1. The chemical shift change $\Delta\delta_{S-R}$ observed using the Mosher method suggested that the absolute configuration of methylated aglycone was a 3'R, 17'R configuration (FIG. 2). In the same way, the remaining compounds 2 and 3 were equally identified.

Absolute Configuration Analysis of Rhamnolipid Compound

Compound 1 (2.0 mg) was dissolved in 3 N HCl (0.5 mL), heated to 100° C. for 2 hours, cooled, and extracted twice with ethyl acetate. The ethyl acetate layer and the aqueous layer provided methylated aglycone (1.4 mg) and a sugar residue (0.4 mg), and the sugar residue was dissolved in pyridine (0.5 mL) containing L-cysteine methyl ester hydrochloride (0.5 mg) and heated at 60° C. for 1 hour. o-tolyl isothiocyanate (10 µL) was added to the mixture which was further heated for 1 hour. The reaction mixture was analyzed directly using HPLC (0.1% formic acid and 10 to 100% gradient of ACN for 40 minutes). The sugar residue of compound 1 was detected at 17.9 minutes. The retention times of pure rhamnose samples under the same HPLC conditions were 15.5 (D-rhamnose) and 17.9 (L-rhamnose). Therefore, it was confirmed that the absolute configuration of rhamnose of compound 1 was L, and the remaining compounds were identified in the same way.

Experimental Example. Identification of Cytotoxicity of Rhamnolipid Compounds Against Cancer Cell Lines Human cancer cell lines HCT-15 (colon cancer), NUGC-3 (gastric cancer), NCI-H23 (liver cancer), ACHN (kidney cancer), PC-3 (prostate cancer) and MDA-MB-231 (breast cancer) were purchased from American Type Culture Collection (Manassas, Va.).

Cancer cell lines were cultured in RPMI 1640 supplemented with 10% fetal bovine serum (FBS) in a 5% $CO_2$ humid atmosphere at 37° C. The evaluation of growth inhibitory ability against human cancer cell lines was performed via the Sulforhodamine B (SRB) method. The cells were dispensed into a 96-well plate at a density of 8,000 cells/well, and the next day, cells were treated with compounds 1 to 3 (0.1% DMSO as vehicle control), and treated with a positive control (adriamycin). After incubation for 48 hours, the culture fluid was fixed with 50% trichloroacetic acid (50 µg/mL) and stained with 0.4% sulforhodamine B contained in 1% acetic acid. The unbound dye was washed with 1% acetic acid, and the dye bound to the protein was extracted with 10 mM Tris base (pH 10.5) to determine the optical density. The absorbance at 540 nm was determined using a VersaMax microplate reader (Molecular Devices, LLC, Sunnyvale, Calif., USA). The $GI_{50}$ values were calculated using GraphPad Prism 4.0 software (GraphPad Software, Inc., San Diego, Calif., USA) and shown in Table 3 below.

TABLE 3

| Cell lines | $GI_{50}$ (µM) [a] | | | |
|---|---|---|---|---|
|  | 1 | 2 | 3 | ADR[b] |
| HCT-15 | 41.5 | 16.7 | 26.9 | 1.4 |
| NUGC-3 | 30.6 | 19.3 | 32.0 | 1.5 |
| NCI-H23 | 27.5 | 13.7 | 36.9 | 1.4 |
| ACHN | 34.2 | 14.1 | 29.1 | 1.3 |
| PC-3 | 37.8 | 18.2 | 33.3 | 1.4 |
| MDA-MB-231 | 30.6 | 40.4 | 25.5 | 1.5 |

[a] The $GI_{50}$ value is a concentration value corresponding to 50% growth inhibition.
[b] adriamycin As shown in Table 3, compounds 1 to 3 exhibited a $GI_{50}$ of 13.7 µM to 41.5 µM, and compound 2 of Example 1 exhibited particularly excellent activity against cancer cell lines.

As described above, details of the present disclosure have been described. Those of ordinary skill in the art may appreciate that the details are only preferred embodiments, and the scope of the present disclosure is not limited thereto. Therefore, the actual scope of the present disclosure is defined by the appended claims and their equivalents.

[Accession Number]

Name of deposit institution: Korea Research Institute of Bioscience and Biotechnology

Accession number: KCTC13780BP

Deposit date: Dec. 20, 2018

The invention claimed is:

1. A rhamnolipid compound of Chemical Formula 1, an optical isomer thereof, or a pharmaceutically acceptable salt thereof:

[Chemical Formula 1]

wherein in Chemical Formula 1, n is 1 or 2, and R is

2. The compound of claim 1, wherein the compound of Chemical Formula 1 is one selected from a group consisting of following compounds:
  17-hydroxy-3-(3,4,5-trihydroxy-6-methyltetrahydro-2H-pyran-2-yloxy)octadecanoic acid;
  17-oxo-3-(3,4,5-trihydroxy-6-methyltetrahydro-2H-pyran-2-yloxy)octadecanoic acid; and
  3-(4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

3. The compound of claim 2, wherein the compound is one selected from a group consisting of following compounds:
  (17R)-17-hydroxy-3-((2S)-3,4,5-trihydroxy-6-methyltetrahydro-2H-pyran-2-yloxy)octadecanoic acid;
  17-oxo-3-((2S)-3,4,5-trihydroxy-6-methyltetrahydro-2H-pyran-2-yloxy)octadecanoic acid; and
  (17R)-3-((2S)-4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

4. A method for preparing a compound of Chemical Formula 1, an optical isomer thereof, or a pharmaceutically acceptable salt thereof,

[Chemical Formula 1]

wherein in Chemical Formula 1, n is 1 or 2, and R is wherein the method comprises separating the compound represented by Chemical Formula 1, the optical isomer thereof or the pharmaceutically acceptable salt thereof from *Actinoalloteichus hymeniacidonis* 179DD-027 KCTC 13780BP strain or a culture thereof.

5. A pharmaceutical composition comprising the rhamnolipid compound of Chemical Formula 1 of claim 1, the optical isomer thereof, or the pharmaceutically acceptable salt thereof.

6. A pharmaceutical composition for treating or preventing cancer, the pharmaceutical composition comprising the rhamnolipid compound of Chemical Formula 1 of claim 1, the optical isomer thereof, or the pharmaceutically acceptable salt thereof.

7. The pharmaceutical composition of claim 6, wherein the cancer includes at least one selected from a group consisting of: pseudomyxoma, intrahepatic biliary tract cancer, hepatoblastoma, liver cancer, thyroid cancer, colorectal cancer, testicular cancer, myelodysplastic syndrome, glioblastoma, oral cancer, cleft lip cancer, mycosis fungoides, acute myelogenous leukemia, acute lymphocytic leukemia, basal cell carcinoma, ovarian cancer, ovarian epithelial carcinoma, ovarian germ cell carcinoma, male breast cancer, brain cancer, pituitary adenoma, multiple myeloma, gallbladder cancer, biliary tract cancer, colon cancer, chronic myelogenous leukemia, chronic lymphocytic leukemia, retinoblastoma, choroidal melanoma, diffuse giant B-cell lymphoma, barter bulge cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, pediatric brain cancer, pediatric lymphoma, pediatric leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, mesothelioma, rectal cancer, rectal carcinoma, vaginal cancer, spinal carcinoma, auditory nerve sheath, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, or thymic cancer.

8. A method for treating cancer comprising administering a therapeutically effective amount of the rhamnolipid compound of Chemical Formula 1 of claim 1, the optical isomer thereof, or the pharmaceutically acceptable salt thereof to a subject in need thereof.

9. The method of claim 8, where the compound of Chemical Formula 1 is one selected from a group consisting of following compounds:
17-hydroxy-3-(3,4,5-trihydroxy-6-methyltetrahydro-2H-pyran-2-yloxy)octadecanoic acid;
17-oxo-3-(3,4,5-trihydroxy-6-methyltetrahydro-2H-pyran-2-yloxy)octadecanoic acid; and
3-(4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

10. The method of claim 8, where the compound of Chemical Formula 1 is one selected from a group consisting of following compounds:
(17R)-17-hydroxy-3-((2S)-3,4,5-trihydroxy-6-methyltetrahydro-2H-pyran-2-yloxy)octadecanoic acid;
17-oxo-3-((2S)-3,4,5-trihydroxy-6-methyltetrahydro-2H-pyran-2-yloxy)octadecanoic acid; and
(17R)-3-((2S)-4,5-dihydroxy-6-methyl-3-(3,4,5-trihydroxy-6-methyltetrahydro-2H-pyran-2-yloxy)tetrahydro-(2H-pyran-2-yloxy)-17-hydroxyoctadecanoic acid.

11. The method of claim 8, wherein the cancer includes at least one selected from a group consisting of: pseudomyxoma, intrahepatic biliary tract cancer, hepatoblastoma, liver cancer, thyroid cancer, colorectal cancer, testicular cancer, myelodysplastic syndrome, glioblastoma, oral cancer, cleft lip cancer, mycosis fungoides, acute myelogenous leukemia, acute lymphocytic leukemia, basal cell carcinoma, ovarian cancer, ovarian epithelial carcinoma, ovarian germ cell carcinoma, male breast cancer, brain cancer, pituitary adenoma, multiple myeloma, gallbladder cancer, biliary tract cancer, colon cancer, chronic myelogenous leukemia, chronic lymphocytic leukemia, retinoblastoma, choroidal melanoma, diffuse giant B-cell lymphoma, barter bulge cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, pediatric brain cancer, pediatric lymphoma, pediatric leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, gastric cancer, gastric carcinoma, gastrointestinal cancer, Wilms cancer, breast cancer, sarcoma, penile cancer, pharyngeal cancer, pregnancy villous disease, cervical cancer, endometrial cancer, uterine sarcoma, prostate cancer, metastatic bone cancer, metastatic brain cancer, mediastinal cancer, mesothelioma, rectal cancer, rectal carcinoma, vaginal cancer, spinal carcinoma, auditory nerve sheath, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, or thymic cancer.

12. The pharmaceutical composition of claim 5, further comprising at least one pharmaceutically acceptable carrier.

* * * * *